US012589233B2

(12) United States Patent
Wheeler et al.

(10) Patent No.: US 12,589,233 B2
(45) Date of Patent: Mar. 31, 2026

(54) BALL VALVE FOR USE IN A RESPIRATION CIRCUIT AND A RESPIRATION CIRCUIT INCLUDING A BALL VALVE

(71) Applicant: Engineered Medical Systems, Inc., Indianapolis, IN (US)

(72) Inventors: Bradley Allen Wheeler, Martinsville, IN (US); Jessica Mae Zinnecker, Indianapolis, IN (US); Kevin Michael Sempsrott, Anderson, IN (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 1225 days.

(21) Appl. No.: 17/483,374

(22) Filed: Sep. 23, 2021

(65) Prior Publication Data

US 2023/0087323 A1     Mar. 23, 2023

(51) Int. Cl.
*A61M 39/24*         (2006.01)
*A61M 16/06*         (2006.01)
(Continued)

(52) U.S. Cl.
CPC ............ *A61M 39/24* (2013.01); *A61M 16/06* (2013.01); *A61M 39/223* (2013.01);
(Continued)

(58) Field of Classification Search
CPC .................. A61M 16/20; A61M 39/24; A61M 2039/248; A61M 11/005; A61M 11/02; A61M 11/04; A61M 16/109; A61M 16/14; A61M 16/0816; A61M 16/0825; A61M 16/0833; A61M 2039/229; F16K 11/0853;
(Continued)

(56) References Cited

U.S. PATENT DOCUMENTS

| | | | | | |
|---|---|---|---|---|---|
| 3,156,260 | A | * | 11/1964 | Harvey | F16K 11/087 |
| | | | | | 251/174 |
| 3,927,693 | A | * | 12/1975 | Johnston | F16K 11/0853 |
| | | | | | 137/625.47 |

(Continued)

FOREIGN PATENT DOCUMENTS

| | | | | | |
|---|---|---|---|---|---|
| CN | 104653817 | A | * | 5/2015 | F16K 11/0873 |
| DE | 19636200 | C1 | * | 7/1997 | F16K 11/0853 |

(Continued)

OTHER PUBLICATIONS

PE2E Translation for Kluth H DE_19636200 (Year: 1997).*

(Continued)

*Primary Examiner* — Victoria Murphy
*Assistant Examiner* — Sydney Reyes Russell
(74) *Attorney, Agent, or Firm* — Woodard, Emhardt, Henry, Reeves & Wagner, LLP

(57)          ABSTRACT

A ball valve for a use in a respiration circuit, including a housing defining a ball chamber. The ball chamber communicating with a gas inlet and at least two gas outlets. A ball received in the ball chamber. The ball being configured for rotation about an axis of rotation within the ball chamber. The channel having a channel inlet configured for selective fluid communication with the gas inlet. The channel inlet being in fluid communication with a channel outlet configured for selective fluid communication with at least one of the at least two gas outlets.

20 Claims, 9 Drawing Sheets

(51) Int. Cl.
  *A61M 39/22* (2006.01)
  *F16K 11/087* (2006.01)

(52) U.S. Cl.
  CPC .... *F16K 11/0873* (2013.01); *A61M 2039/229* (2013.01); *A61M 2039/248* (2013.01)

(58) Field of Classification Search
  CPC .. F16K 11/087; F16K 11/0873; F16K 11/022; F16K 11/025; F16K 11/085–11/0856
  See application file for complete search history.

(56)               References Cited

U.S. PATENT DOCUMENTS

| | | | | |
|---|---|---|---|---|
| 3,957,082 | A * | 5/1976 | Fuson | A61M 39/223 604/80 |
| 4,031,918 | A * | 6/1977 | Cagle | F16K 11/0853 251/317 |
| 4,881,718 | A * | 11/1989 | Champagne | F16K 5/0605 251/316 |
| 4,904,245 | A * | 2/1990 | Chen | A61M 3/0233 604/248 |
| 5,251,663 | A * | 10/1993 | Christianson | F16K 11/0853 251/214 |
| 5,443,453 | A * | 8/1995 | Walker | A61M 39/223 604/32 |
| 5,466,228 | A * | 11/1995 | Evans | F16K 11/0853 604/32 |
| 5,911,405 | A * | 6/1999 | Korczynski, Jr. | F16K 27/067 251/315.11 |
| 5,944,055 | A * | 8/1999 | Dicky | F16K 11/0873 251/148 |
| 6,539,899 | B1 * | 4/2003 | Piccirilli | F01P 7/167 123/41.1 |
| 7,278,449 | B2 * | 10/2007 | Mueller | F16K 11/0853 277/432 |
| 8,052,656 | B2 * | 11/2011 | Dorsey | A61M 39/223 604/246 |
| 8,584,701 | B2 * | 11/2013 | Duncan | A61M 39/223 116/277 |
| 9,050,434 | B2 | 6/2015 | Faram | |
| 9,470,325 | B2 * | 10/2016 | DeRosa | F16K 11/0856 |
| 10,544,903 | B2 * | 1/2020 | Ikeda | F17C 13/04 |
| 11,160,948 | B2 * | 11/2021 | Mansi | A61M 16/0683 |
| 11,193,599 | B2 * | 12/2021 | Wintch | F16K 11/0873 |
| 2005/0061318 | A1 | 3/2005 | Faram | |
| 2005/0247313 | A1 * | 11/2005 | Niles | A61M 16/0875 128/203.16 |
| 2006/0065313 | A1 * | 3/2006 | Saleri | F16K 5/0605 137/625.41 |
| 2008/0000472 | A1 * | 1/2008 | Wall | A61M 16/20 128/205.24 |
| 2010/0074881 | A1 | 3/2010 | Boucher et al. | |
| 2011/0214673 | A1 | 9/2011 | Masionis | |
| 2014/0053931 | A1 * | 2/2014 | Whitaker | F16K 11/0853 137/625.17 |
| 2018/0087501 | A1 * | 3/2018 | Hopkins | F16K 27/065 |

FOREIGN PATENT DOCUMENTS

| | | | | |
|---|---|---|---|---|
| DE | 102014208358 | A1 * | 11/2015 | F16K 11/0873 |
| EP | 3680523 | A1 * | 7/2020 | F01P 7/14 |

OTHER PUBLICATIONS

PE2E Translation for Liu CN_104653817 (Year: 2015).*
PE2E Translation for Haj H A DE_102014208358 (Year: 2015).*
PE2E Translation Liu CN_104653817_A_H (Year: 2015).*

* cited by examiner

BALL VALVE FOR USE IN A RESPIRATION CIRCUIT AND A RESPIRATION CIRCUIT INCLUDING A BALL VALVE

COPYRIGHT STATEMENT

TECHNICAL FIELD

The present disclosure is directed to a respiration circuit, and more particularly to a ball valve for use in a respiration circuit and a respiration circuit including a ball valve.

BACKGROUND

Respiration circuits are used in a variety of respiratory therapies. In some instances, respiratory therapies require a pressurized gas supply to two or more devices. For example, when a patient is receiving CPAP, particularly on an ongoing basis, humidifying the pressurized gas delivered to the patient by means of a nebulizer can increase patient comfort and help protect sensitive tissue from drying out. For other therapies, a nebulizer can be useful for administering nebulized medications to a patient receiving respiratory support. These therapies typically require two separate sources of pressurized gas be provided, or a Y-splitter from a single source be provided in the respiration circuit. Providing two sources of pressurized gas can be difficult in a home setting and complicates the circuit. A Y-splitter has the limitation that if the gas supply needs to be terminated in one but not both of the devices, the gas supply must be cut off to both at least temporarily to remove the Y-splitter, which is awkward, time consuming and can prove uncomfortable or even harmful to the patient.

The present invention is directed toward overcoming one or more of the problems discussed above.

SUMMARY OF THE EMBODIMENTS

A first aspect of the disclosure is a ball valve for a use in a respiration circuit. In one embodiment the ball valve includes a housing defining a ball chamber, the ball chamber communicating with a gas inlet and at least two gas outlets. A ball is received in the ball chamber, the ball being configured for rotation about an axis of rotation within the ball chamber. The ball has a channel extending perpendicular to the axis of rotation, the channel terminating in a channel inlet configured for fluid communication with the gas inlet. The channel inlet is in fluid communication with a channel outlet configured for selective fluid communication with each of the at least two gas outlets. An actuator is configured to rotate the ball about the axis of rotation. The actuator can rotate the ball to a first position with the gas inlet in fluid communication with the channel inlet and the channel outlet in fluid communication with each of the at least two gas outlets, a second position with the gas inlet in fluid communication with the channel inlet and the gas outlet in fluid communication with only one gas outlet of the at least two gas outlets, and a third position with the gas inlet in fluid communication with the channel inlet and the gas outlet in fluid communication with at least one other gas outlet of the at least two gas outlets.

Various embodiments can be limited to two gas outlets. In such embodiments each of the two outlets can have different sized cross-sections to facilitate different rates of flow volumes through the respective gas outlets. Various embodiments can include the actuator being configured to rotate the ball to a fourth position with the gas inlet not in fluid communication with the channel inlet. In various embodiments, the actuator comprises a stem extending from the ball along the axis of rotation and a handle operatively associated with a distal end of the stem. Various embodiments can include a first elastomeric O-ring surrounding the gas inlet between a surface of the ball chamber and a surface of the ball, a second elastomeric O-ring surrounding one of the at least two gas outlets between the surface of the ball chamber and the surface of the ball, a third elastomeric O-ring surrounding at least one other of the at least two gas outlets between the surface of the ball chamber and the surface of the ball. In such embodiments in the first position the channel inlet is at least partially within a circumference of the first O-ring and the channel outlet is at least partially within the a circumference of the second O-ring and the third O-ring; in the second position the channel inlet is at least partially within the circumference of the first O-ring and the channel outlet is at least partially within the circumference of the second O-ring and the channel outlet is completely outside the circumference of the third O-ring; and in the third position the channel inlet is at least partially within the circumference of the first O-ring and the channel outlet is at least partially within the circumference of the third O-ring and channel outlet is completely outside the circumference of the second O-ring. In embodiments including a fourth position of the actuator, the channel inlet is completely outside the circumference of the first O-ring. In various embodiments the channel is elliptical with the major axis perpendicular to the axis of rotation and the major axis in channel inlet being shorter than the major axis in the channel outlet. Embodiments can also include a fourth elastomeric O-ring surrounding the first elastomeric O-ring and the gas inlet between a surface of the ball chamber and a surface of the ball positioned to prevent gas flow between the ball surface and a ball chamber surface outside the circumference of the fourth elastomeric O-ring with the ball in any of the first, second, third or fourth positions and a fifth elastomeric O-ring surrounding the second and third elastomeric O-rings and each of the at least two gas outlets between the surface of the ball chamber and the surface of the ball positioned to prevent gas flow between the ball surface and the ball chamber surface outside the circumference of the fifth elastomeric O-ring with the ball in any of the first, second, third or fourth positions.

Another aspect of the invention is a respiration circuit system including a ball valve incorporating one or more of the various embodiments discussed above. The respiration circuit system further includes a mask having a mask inlet, the mask inlet being in fluid communication with the one gas outlet of the at least two gas outlets and a nebulizer having nebulizer inlet and a nebulizer outlet, the nebulizer inlet being in fluid communication with the at least one other gas outlet of the at least two gas outlets and the nebulizer outlet being in fluid communication with the mask.

Various modifications and additions can be made to the embodiments discussed without departing from the scope of the invention. For example, while the embodiments described above refer to particular features, the scope of this invention also included embodiments having different combination of features and embodiments that do not include all of the above-described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described and claimed herein, and while various features are ascribed to different embodiments, it should be appreciated that the features described with respect to one embodiment may be incorporated with other embodiments as well. By the same token, however, no single feature or features of any described or claimed embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
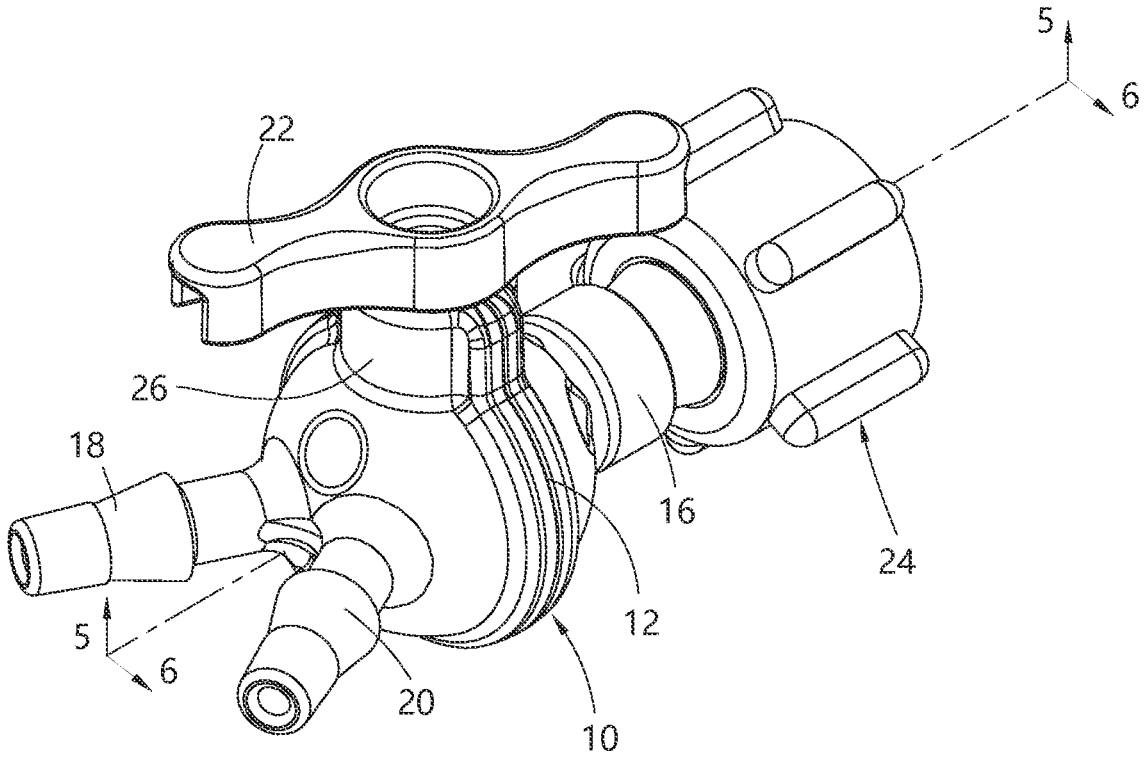
FIG. 1 is a perspective view of ball valve for use in a respiration circuit in accordance with the present disclosure with a threaded connector attached to an gas inlet of the ball valve.

FIG. 1 shows a ball-valve 10 for use in a respiration circuit having a housing 12 defining a ball chamber 14 (see FIG. 2) in fluid communication with a gas inlet 16, a first barbed gas outlet 18 and second barbed gas outlet 20. A handle 22 protrudes from a top of the housing. In the illustrated embodiment, and optional threaded connector 24 is attached to the gas inlet 16 of the ball-valve 10 for connection to a pressurized gas supply (see FIG. 9).

Figure 2:
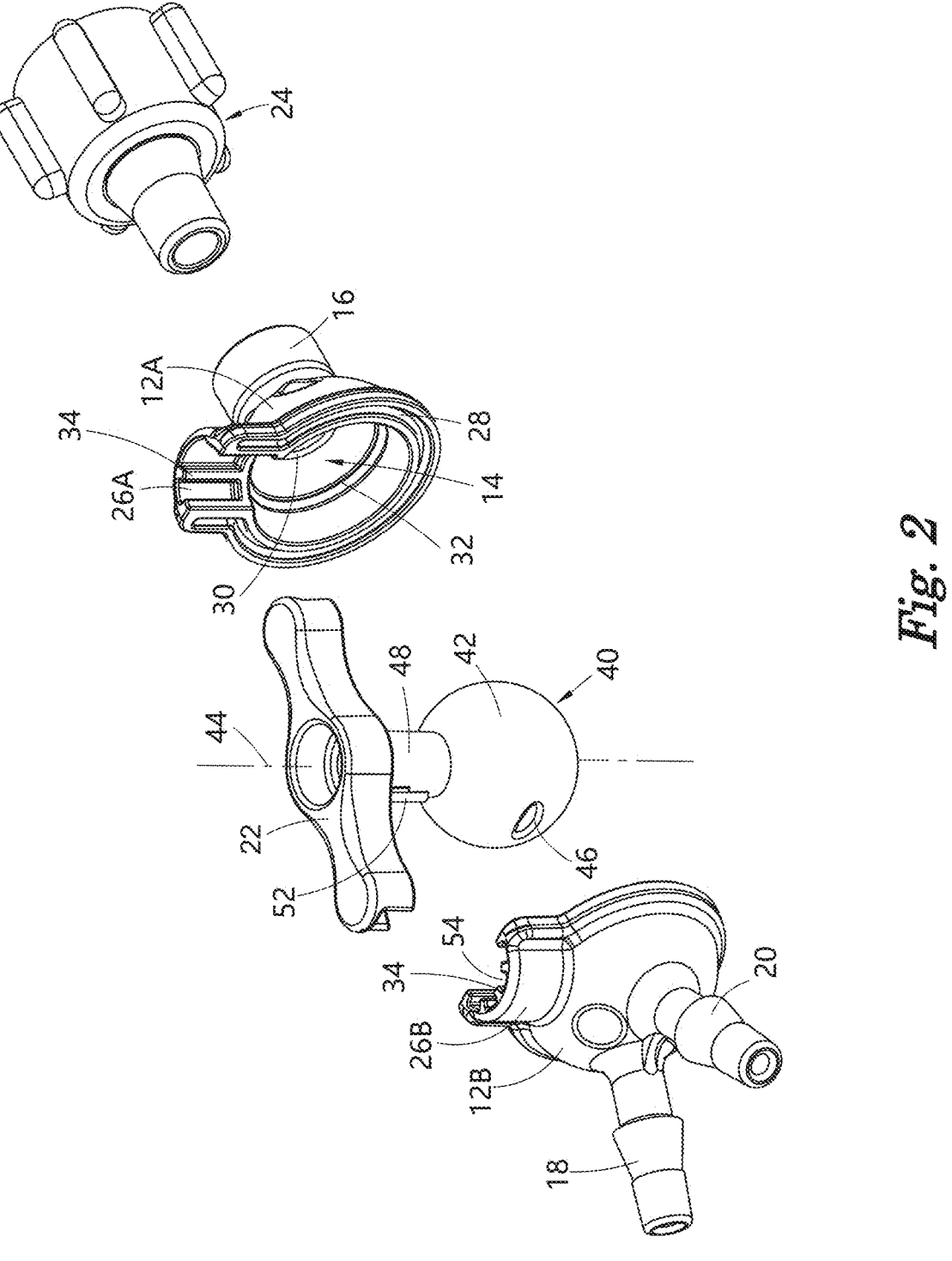
FIG. 2 is an exploded view of the ball valve and quick-connect adapter of FIG. 1.
Figure 3:
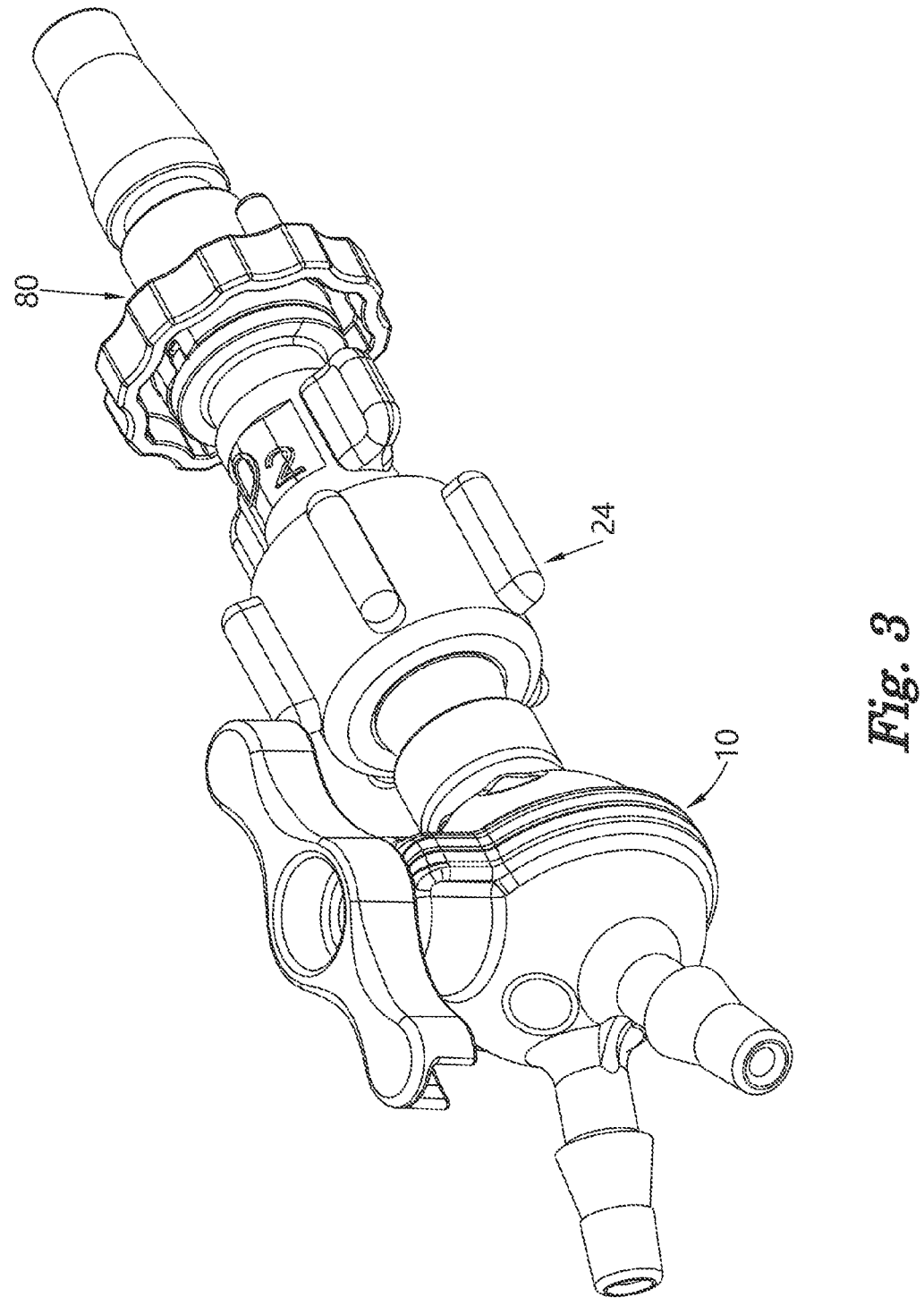
FIG. 3 is a perspective view of the ball valve with a threaded connector attached to an gas inlet of FIG. 1 further including a quick-connect fitting attached to the threaded connector.
Figure 4:
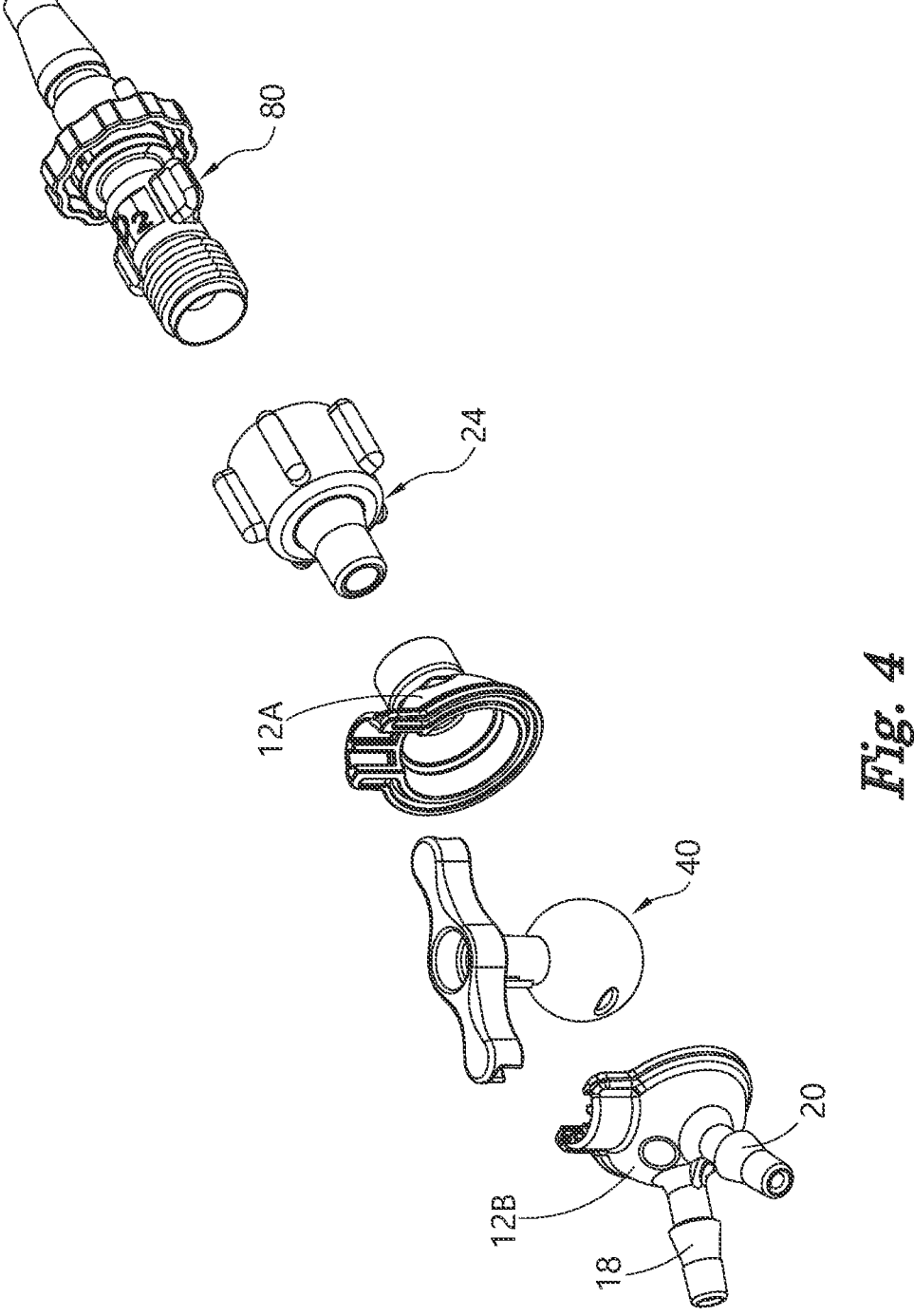
FIG. 4 is an exploded view of the assembly of FIG. 3.

The ball valve 10 is shown in greater detail in the exploded view of FIG. 2. In the illustrated embodiment, the housing 12 comprises an inlet side 12A and an outlet side 12B defining the ball chamber 14. The gas inlet 16 extends from the inlet side 12A and the first and second barbed gas outlets 18, 20 extend from the outlet side 12B substantially opposite the gas inlet 16. The inlet side 12A and the outlet side 12B further define a bearing collar 26 by mating of inlet side collar part 26A and outlet side collar part 26B. About the periphery of the inlet side 12A, the outlet side 12B, and inlet and outlet side collar parts 26A and 26B are mating flanges 28 for connection of the inlet and outlet sides 12A, 12B. Also visible in FIG. 2, within the ball chamber surface 30 are a number of channels 32 for receiving O-rings, as will be discussed below. Extending inwardly from the collar parts 26A and 26B are support flanges 34 that will be discussed in greater detail below.

A ball assembly 40 includes a ball 42 rotatable about an axis of rotation 44 when received in the ball chamber 14. A channel 46 extends through the ball 42 transverse to the axis of rotation 44; in some embodiments the channel extends perpendicular to the axis of rotation, in the manner illustrated herein. A stem 48 extends from the ball 42 along the axis of rotation 44 with a handle 22 attached to its distal end. As should be apparent from FIG. 2, the ball 42 is received in the ball chamber 14 with the stem 48 of the ball assembly 40 received in the collar 26. The handle 22 acts as an actuator for rotating the ball 42 about the axis of rotation 44. A protrusion 52 extends radially from the stem for engaging alignment detents 54 formed by the support flanges 34 extending radially inwardly from an inside surface of the collar 26.

Referring to FIGS. 5A-D, the channel 46 has a small cross-section channel segment 46A terminating in a channel inlet 60 configured for selective fluid communication with the gas inlet 16, the small cross-section channel segment 46A being in fluid communication with a large cross-section channel segment 46B terminating in a channel outlet 62. In the illustrated embodiment, the channel has an elliptical cross-section (see FIGS. 2, 4, 7 and 8) with a major axis perpendicular to the axis of rotation 44 and a shorter minor axis parallel to the axis of rotation 44. The major axis in the small cross-section channel segment 46A is shorter than the major axis in the large cross-section channel segment 46B. Alternatively, the channel 46 may be provided with a more uniform transition between the relatively small channel inlet 60 and the relatively large channel outlet 62. Other alternative embodiments could have the cross-sectional segments 46A and 46B as well as the channel inlet 60 and the channel outlet 62 being of the same size and configuration. In other words, in such embodiments the channel 46, the channel inlet 60 and the channel outlet 62 have a uniform cross section between and including the channel inlet 60 and the channel outlet 62.

Figure 5A:
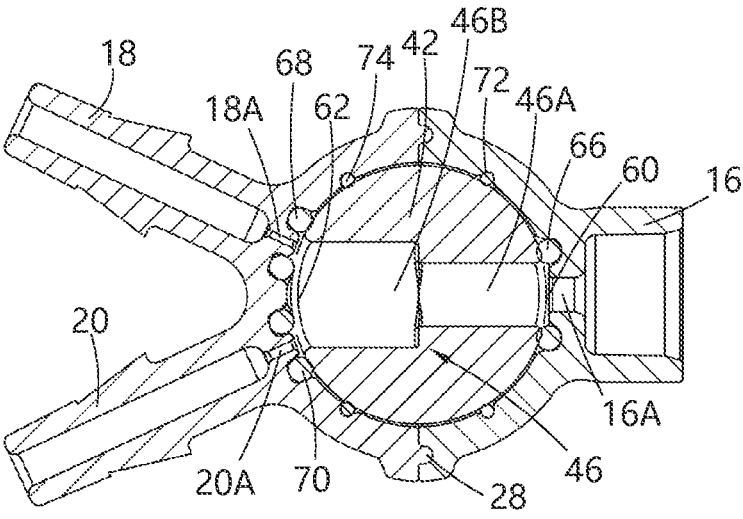
FIGS. 5A-5D are cross-sectional views of the ball valve of FIG. 1 taken along line 5-5 of FIG. 1 showing the ball in first, second, third and fourth positions, respectively.
Figure 5B:
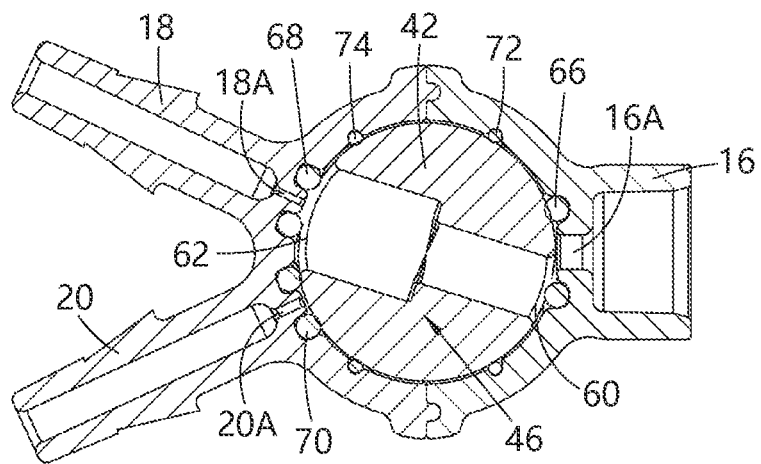
Figure 5C:
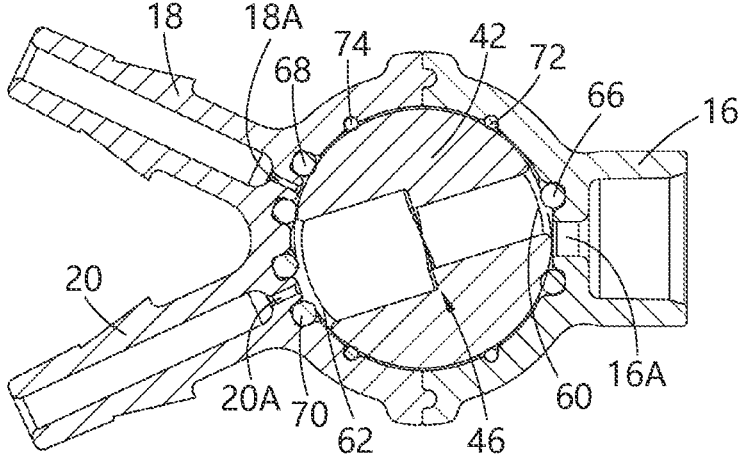

A number of O-rings are provided between the surface 30 of the ball chamber 14 and the ball 42. In the illustrated embodiment, these O-rings reside in correspondingly shaped O-ring channels 32 formed in the surface 30 of the ball chamber 14. Referring to FIG. 5A, a first elastomeric O-ring 66 surrounds the gas inlet 16, more particularly, an inlet nozzle 16A; a second elastomeric O-ring 68 surrounds the first gas outlet 18, more particularly a first outlet nozzle 18A; a third elastomeric O-ring 70 surrounds a second gas outlet 20, more particularly the second outlet nozzle 20A; a fourth elastomeric O-ring 72 surrounds the first elastomeric O-ring 66 to prevent gas flow between the ball surface and the ball chamber surface 30 outside the circumference of the fourth elastomeric O-ring 72 in any of the positions discussed below; and a fifth elastomeric O-ring 74 surrounds the second and third elastomeric O-rings 68, 70 and each of the gas outlet nozzles 18A and 20A, positioned to prevent gas flow between the ball surface and the ball 42 and the chamber surface 30 outside the circumference of the fifth elastomeric O-ring 74 in any of the positions discussed below.

The various components described above (excepting the O-rings) can be made of any suitable plastic using injection molding, machining, or any other suitable process. Non-limiting examples of plastics include acetal and acrylonitrile butadiene styrene (ABS). The O-rings can be made of numerous elastomeric materials, including silicone or rubber compositions, and optionally can be coated with a non-stick material such as polytetrafluoroethylene (PTFE), commonly known by the brand name Teflon®, or a lubricant. The assembled ball valve shown in various figures is held together by known processes such as sonic welding or solvent bonding, and the assembly is facilitated by the mating flanges 28 (see FIGS. 5A-D).

Figure 5D:
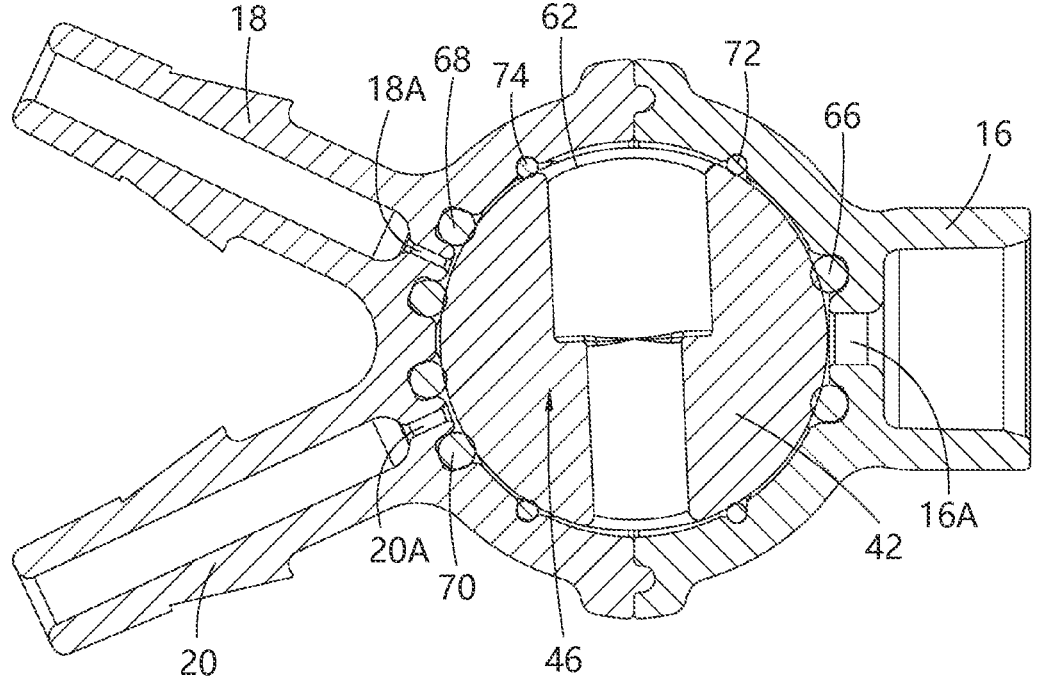
Figure 6:
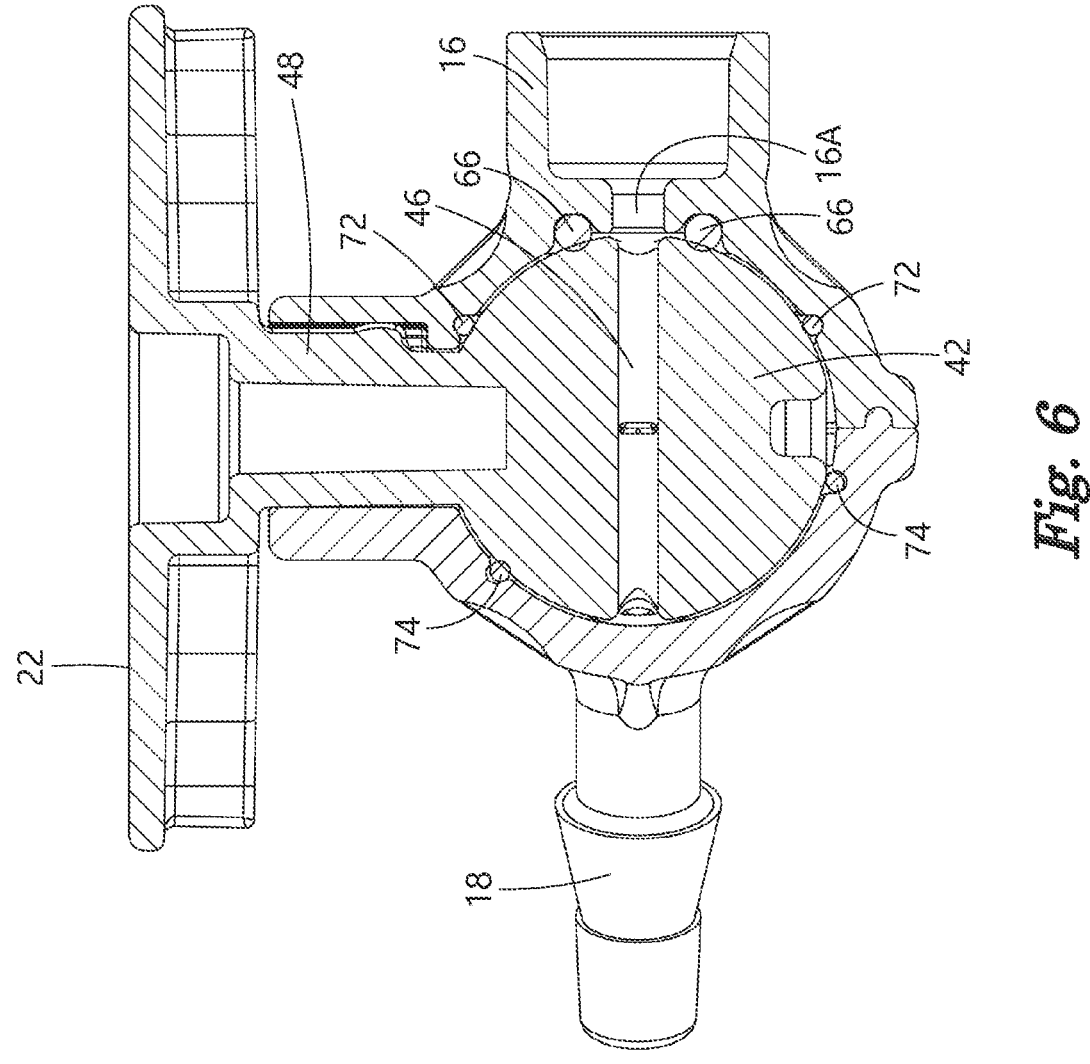
FIG. 6 is a cross-sectional view of the ball valve of FIG. 1 taken along line 6-6 of FIG. 1 showing the ball in the first position.
Figure 7:
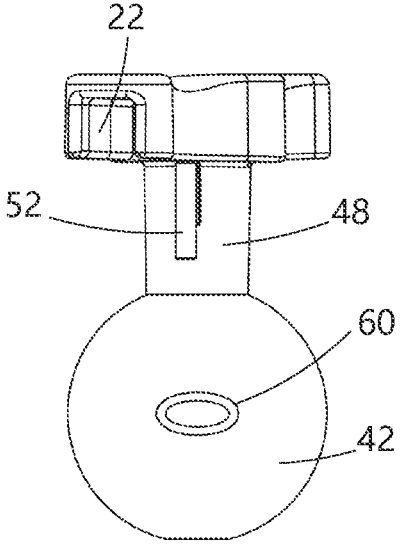
FIG. 7 is a front elevation view of the ball assembly if FIG. 2 showing a ball channel inlet.
Figure 8:
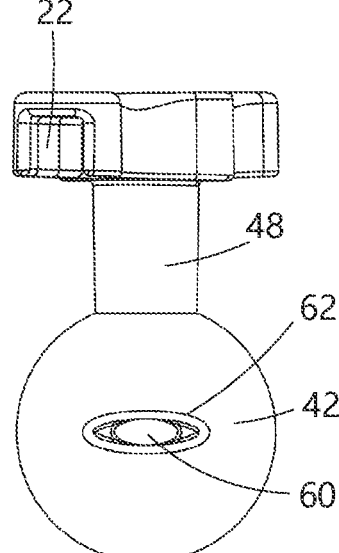
FIG. 8 is a rear elevation view of the ball assembly of FIG. 1 showing a ball channel outlet.

Referring to FIGS. 5A-D, the ball valve 10 is configured to operate as follows. By turning the handle 22 the ball 42 is rotated or actuated to several different positions. In a first position shown in FIG. 5A, the channel inlet 60 is at least partially within a circumference of the first O-ring 66 and the channel outlet 62 is at least partially within a circumference of the second O-ring 68 and the third O-ring 70. In a second position shown in FIG. 5B, the channel inlet 60 is at least partially within the circumference of the first O-ring 66, the channel outlet 62 is at least partially within the circumference of the second O-ring 68, and the channel outlet 62 is completely outside the circumference of the third O-ring 70. In a third position illustrated in FIG. 5C, the channel inlet 60 is at least partially within the circumference of the first O-ring 66, the channel outlet 62 is at least partially within the circumference of the third O-ring 70 and channel outlet 62 is completely outside the circumference of the second O-ring 68. In a fourth position illustrated in FIG. 5D, the gas inlet 16 is not in fluid communication with the channel inlet 60 because the channel inlet 60 is completely outside the circumference of the first O-ring 66, preventing gasflow through ball valve 10. As shown in FIG. 5D, the channel outlet 62 is also completely outside the circumference of the second and third O-rings 68, 70.

Embodiments of the ball valve 10 can include the protrusion 52 from the stem 48 to function in cooperation with the placement of the parallel flanges 56 as detents to nest between adjacent parallel flanges to seat the valve in a select one of the different positions. Embodiments could also be configured to prevent rotation of the handle to a position such as the fourth position described above stopping flow through the valve, depending upon the application of the ball valve 10.

As illustrated in FIGS. 5A-D, the nozzle 18A of the first gas outlet 18 is of a smaller diameter than the nozzle 20A of the second gas outlet 20. The diameters can be chosen to provide a select lower flow rate from the first gas outlet than the second gas outlet. Alternatively, both nozzles 18A and 20A could have the same diameter to provide the same flow rate. In certain embodiments, a pressurized gas flow source communicating with the gas inlet 16 has a standard pressure and flow rate allowing the flow rate and pressure through the first and second gas outlets 18, 20 to be substantially calibrated for select applications, as will be illustrated in the Example below. It should also be noted that various embodiments could include more than two gas outlets and the components could be modified consistent with the operational principles discussed above to provide various combinations of flow from the various gas outlets at varying relative flow rates.

Embodiments could include the ball valve 10 being a disposable that would be useful for infection control in a clinical setting. For example, embodiments with calibrated hole sizes could make the use of reusable flow meters unnecessary, thus eliminating reusable flow meters a source of infection.

EXAMPLE

The following example is provided for illustrative purposes only and is not intended to limit the scope of the invention.

Example 1

Figure 9:
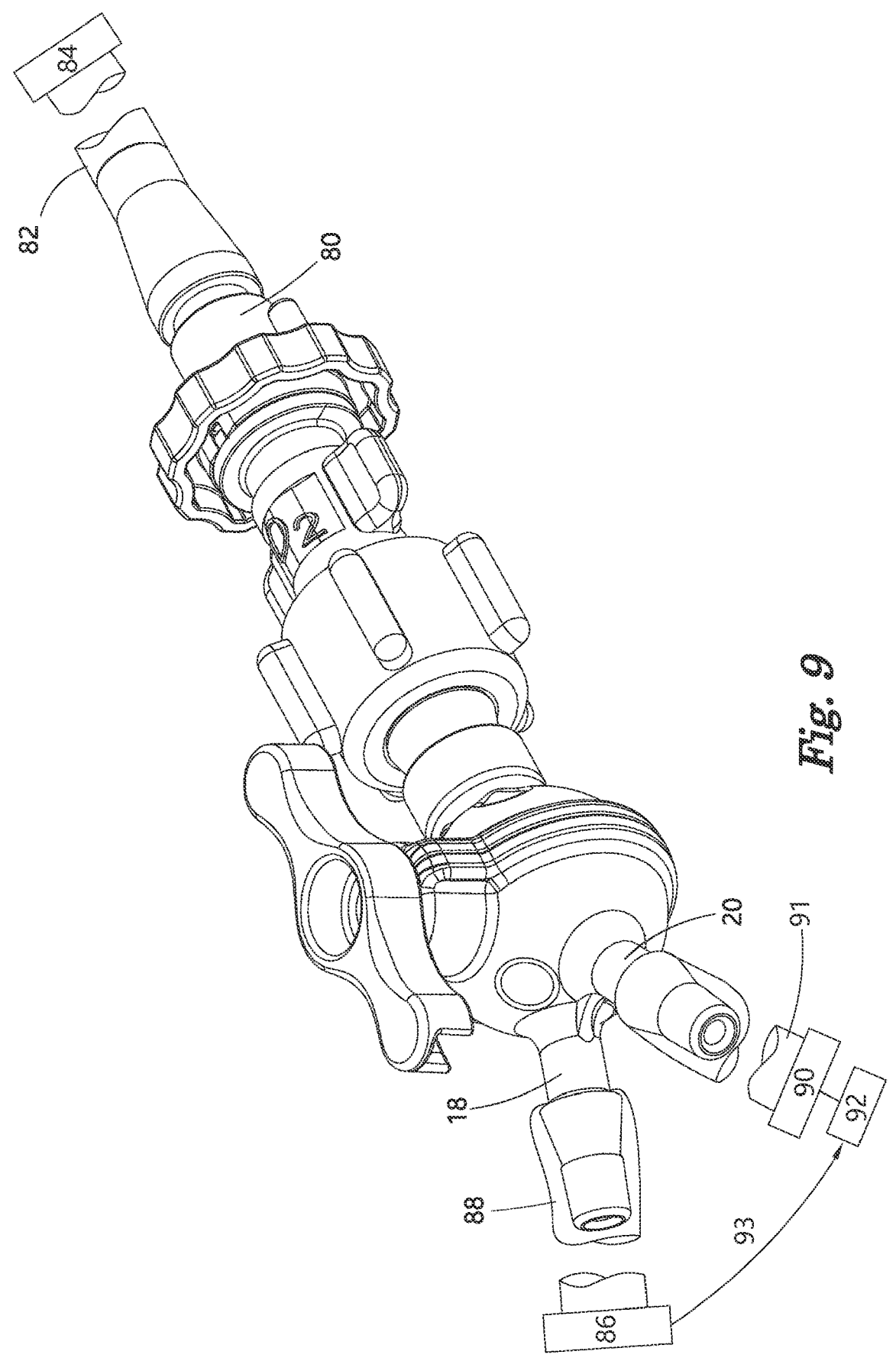
FIG. 9 is a schematic representation of an example of a respiration circuit system, the example of the system including a including the ball valve with a threaded connector attached to an gas inlet and a quick-connect fitting attached to the threaded connector as shown in FIG. 4 and further including a mask, nebulizer and connecting hoses.

FIG. 9 schematically represents an application of the ball valve 10 as part of a respiration circuit system. The ball valve 10 has a threaded connector 24 mated to the gas inlet 16. A quick-connect fitting 80 is attached to the threaded connector 24 and hose 82 runs between the quick-connect fitting 80 and a pressurized gas supply 84 to provide fluid communication therebetween. Embodiments could include the quick-connect fitting 80 attaching directly to the pressurized gas supply 84 without the hose 82. The first gas outlet 18 is in fluid communication with a nebulizer 86, for example, via hose 88. The second gas outlet 20 is in fluid communication with a flow generator 90 inlet, for example, via hose 91. The flow generator may in turn be in fluid communication with a breathing mask 92 which may be, for example, a CPAP mask. Various intermediate components such as a pressure regulator or sensors may be in fluid communication between the gas outlet 20 and the flow generator 90, but any such components are omitted for clarity. An output of the nebulizer 86 is in fluid communication with the breathing mask via hose 93. The combined output of the nebulizer 86 and the second gas outlet can be delivered to a patient by the breathing mask 92. Certain embodiments can have the outlet nozzles configured to provide a flow rate of 15 liters per minute directly to the flow generator 90 and 10 liters per minute to the nebulizer 86 with the pressurized gas at a standard 50 PSI.

Another application of a ball valve 10 in accordance with this disclosure is with a resuscitator bag that requires front end oxygenation as well as oxygen for an accumulator bag.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

What is claimed is:

1. A ball valve for use in a respiration circuit, comprising:
a housing defining a ball chamber, the ball chamber communicating with a single gas inlet and at least two gas outlets;
a ball received in the ball chamber, the ball being configured for rotation about an axis of rotation within the ball chamber, the ball having a channel extending transverse to the axis of rotation, the channel having a channel inlet configured for selective fluid communication with the single gas inlet, the channel inlet being in fluid communication with a channel outlet configured for selective fluid communication with at least one of the at least two gas outlets, wherein the channel inlet has a smaller cross-sectional area than the channel outlet;
an actuator configured to rotate the ball about the axis of rotation, wherein the actuator can rotate the ball to a first position with the single gas inlet in fluid communication with the channel inlet and the channel outlet in fluid communication with each of the at least two gas outlets, a second position with the single gas inlet in fluid communication with the channel inlet and the channel outlet in fluid communication with only one gas outlet of the at least two gas outlets, and a third position with the single gas inlet in fluid communication with the channel inlet and the channel outlet in fluid communication with at least one other gas outlet of the at least two gas outlets.

2. The ball valve of claim 1 wherein the actuator can rotate the ball to a fourth position with the single gas inlet not in fluid communication with the channel inlet.

3. The ball valve of claim 1 wherein the actuator comprises a stem extending from the ball along the axis of rotation and a handle operatively associated with a distal end of the stem.

4. The ball valve of claim 1 further comprising:
a first elastomeric O-ring surrounding the single gas inlet between a surface of the ball chamber and a surface of the ball:
a second elastomeric O-ring surrounding one of the at least two gas outlets between the surface of the ball chamber and the surface of the ball;
a third elastomeric O-ring surrounding a least one other of the at least two gas outlets between the surface of the ball chamber and the surface of the ball;
wherein in the first position the channel inlet is at least partially within a circumference of the first O-ring and the channel outlet is at least partially within a circumference of the second O-ring and the third O-ring; in the second position the channel inlet is at least partially within the circumference of the first O-ring and the channel outlet is at least partially within the circumference of the second O-ring and the channel outlet is completely outside the circumference of the third O-ring; and in the third position the channel inlet is at least partially within the circumference of the first O-ring and the channel outlet is at least partially within the circumference of the third O-ring and channel outlet is completely outside the circumference of the second O-ring.

5. The ball valve of claim 4 wherein the actuator can rotate the ball to a fourth position with the single gas inlet not in fluid communication with the channel inlet, wherein in the fourth position the channel inlet is completely outside the circumference of the first O-ring.

6. The ball valve of claim 5 further comprising:
a fourth elastomeric O-ring surrounding the first elastomeric O-ring and the single gas inlet between a surface of the ball chamber and a surface of the ball positioned to prevent gas flow between the ball surface and the ball chamber surface outside a circumference of the fourth elastomeric O-ring with the ball in any of the first, second, third or fourth positions; and
a fifth elastomeric O-ring surrounding the second and third elastomeric O-rings and each of the at least two gas outlets between the surface of the ball chamber and the surface of the ball positioned to prevent gas flow between the ball surface and the ball chamber surface outside a circumference of the fifth elastomeric O-ring with the ball in any of the first, second, or third positions.

7. The ball valve of claim 6 further comprising a channel formed in the ball chamber surface for receiving each of elastomeric O-rings.

8. The ball valve of claim 1, wherein the channel, the channel inlet and the channel outlet are each elliptical.

9. The ball valve of claim 8 wherein the channel has a major axis perpendicular to the axis of rotation and a shorter minor axis parallel to the axis of rotation, wherein the major axis in the small cross-section channel inlet is shorter than the major axis in the large cross-section channel outlet.

10. The ball valve of claim 1 wherein the only one gas outlet of the at least two gas outlets and the at least one other gas outlet of the at least two gas outlets have different sized nozzle cross-sections to facilitate different rates of flow volumes through the respective gas outlets.

11. The ball valve of claim 1 wherein the housing further comprises a barbed tube radiating from an exterior of the housing about each of the at least two gas outlets.

12. The ball valve of claim 1 wherein the at least two gas outlets comprises two gas outlets.

13. A respiration circuit system comprising:
a ball valve comprising:
a housing defining a ball chamber, the ball chamber communicating with a gas inlet and at least two gas outlets;
a ball received in the ball chamber, the ball being configured for rotation about an axis of rotation within the ball chamber, the ball having a channel extending transverse to the axis of rotation, the channel having a channel inlet configured for selective fluid communication with the gas inlet, the channel inlet being in fluid communication with a channel outlet configured for selective fluid communication with at least one of the at least two gas outlets, wherein the channel inlet has a smaller cross-sectional area than the channel outlet; and an actuator configured to rotate the ball about the axis of rotation, wherein the actuator can rotate the ball to a first position with the gas inlet in fluid communication with the channel inlet and the channel outlet in fluid communication with each of the at least two gas outlets, a second position with the gas inlet in fluid communication with the channel inlet and the channel outlet in fluid communication with only one gas outlet of the at least two gas outlets, and a third position with the gas inlet in fluid communication with the channel inlet and the channel outlet in fluid communication with at least one other gas outlet of the at least two gas outlets;

a mask having a mask inlet, the mask inlet being in fluid communication with the one gas outlet of the at least two gas outlets; and a nebulizer having a nebulizer inlet and a nebulizer outlet, the nebulizer inlet being in fluid communication with the at least one other gas outlet of the at least two gas outlets and the nebulizer outlet being in fluid communication with the mask.

14. The respiration circuit system of claim 13 wherein the one gas outlet of the at least two gas outlets and the other gas outlet of the at least two gas outlets have a nozzle of different cross-sectional areas.

15. The respiration circuit system of claim 14 wherein the nozzle of the one gas outlet the nozzle of the at least two gas outlets has a larger cross-sectional area than the nozzle of the other gas outlet of the at least two gas outlets.

16. The respiration circuit system of claim 13, wherein the channel, the channel inlet and the channel outlet are each elliptical.

17. The respiration circuit system of claim 16 wherein the channel has a major axis perpendicular to the axis of rotation and a shorter minor axis parallel to the axis of rotation, wherein the major axis in the channel inlet is shorter than the major axis in the channel outlet.

18. A valve for use in a respiration circuit, comprising:
a housing defining a chamber, the chamber communicating with a single gas inlet and at least two gas outlets; and
a channel extending through the chamber, the channel having a channel inlet configured for selective fluid communication with the single gas inlet, the channel inlet being in fluid communication with a channel outlet configured for selective fluid communication with at least one of the at least two gas outlets, wherein the channel inlet has a smaller cross-sectional area than the channel outlet;

wherein the channel is movable between at least three positions, wherein in a first position the single gas inlet is in fluid communication with the channel inlet and the channel outlet in fluid communication with each of the at least two gas outlets, wherein in a second position the single gas inlet is in fluid communication with the channel inlet and the channel outlet in fluid communication with only one gas outlet of the at least two gas outlets, and wherein in a third position the single gas inlet is in fluid communication with the channel inlet and the channel outlet is in fluid communication with at least one other gas outlet of the at least two gas outlets.

19. The valve for use in a respiration circuit of claim 18, further comprising a ball received in the chamber, the ball being configured for rotation about an axis of rotation within the chamber, the ball defining the channel, wherein the channel extends transverse to the axis of rotation.

20. The valve for use in a respiration circuit of claim 18, wherein the channel is movable to a fourth position with the single gas inlet not in fluid communication with the channel inlet.

* * * * *